United States Patent
Nagasaki et al.

(10) Patent No.: US 9,962,469 B2
(45) Date of Patent: May 8, 2018

(54) ADHESION-PREVENTING PREPARATION COMPRISING COMPOSITION COMPRISING POLYCATIONIC TRIBLOCK COPOLYMER AND POLYANIONIC POLYMER

(71) Applicant: UNIVERSITY OF TSUKUBA, Ibaraki (JP)

(72) Inventors: Yukio Nagasaki, Ibaraki (JP); Hiroyuki Nakagawa, Ibaraki (JP)

(73) Assignee: UNIVERSITY OF TSUKUBA, Ibaraki (JP)

( * ) Notice: Subject to any disclaimer, the term of this patent is extended or adjusted under 35 U.S.C. 154(b) by 57 days.

(21) Appl. No.: 15/116,577

(22) PCT Filed: Jan. 27, 2015

(86) PCT No.: PCT/JP2015/052146
§ 371 (c)(1),
(2) Date: Aug. 4, 2016

(87) PCT Pub. No.: WO2015/118993
PCT Pub. Date: Aug. 13, 2015

(65) Prior Publication Data
US 2016/0346438 A1 Dec. 1, 2016

(30) Foreign Application Priority Data

Feb. 5, 2014 (JP) ................................ 2014-020211
Aug. 19, 2014 (JP) ................................ 2014-166730

(51) Int. Cl.
| | | |
|---|---|---|
| *A61K 9/00* | (2006.01) |
| *A61L 31/04* | (2006.01) |
| *A61L 31/14* | (2006.01) |
| *A61K 49/00* | (2006.01) |
| *C08F 283/06* | (2006.01) |
| *C08L 5/08* | (2006.01) |
| *C08L 33/02* | (2006.01) |
| *C08L 51/08* | (2006.01) |

(52) U.S. Cl.
CPC ........ *A61L 31/041* (2013.01); *A61K 49/0004* (2013.01); *A61L 31/145* (2013.01); *C08F 283/06* (2013.01); *C08L 5/08* (2013.01); *C08L 33/02* (2013.01); *C08L 51/08* (2013.01); *C08L 2203/02* (2013.01)

(58) Field of Classification Search
None
See application file for complete search history.

(56) References Cited

FOREIGN PATENT DOCUMENTS

| | | |
|---|---|---|
| JP | 3-295561 | 12/1991 |
| JP | 2000-116765 | 4/2000 |
| JP | 2003-19194 | 1/2003 |
| WO | 92/20746 | 11/1992 |
| WO | 02/102864 | 12/2002 |
| WO | 2007/124132 | 11/2007 |
| WO | 2009/078492 | 6/2009 |
| WO | 2009/133647 | 11/2009 |
| WO | 2013/111801 | 8/2013 |
| WO | 2014/199982 | 12/2014 |

OTHER PUBLICATIONS

Extended European Search Report dated Sep. 15, 2017 in European Application No. 15747041.0.
International Search Report dated Apr. 28, 2015 in corresponding International (PCT) Application No. PCT/JP2015/052146.

*Primary Examiner* — James W Rogers
(74) *Attorney, Agent, or Firm* — Wenderoth, Lind & Ponack, L.L.P.

(57) ABSTRACT

[Problem] To provide a composition capable of effectively preventing adhesion.
[Solution] An adhesion-preventing preparation comprising, as an active ingredient, a composition comprising an A-B-A triblock copolymer, in which A denotes a cationically chargeable polymer block and B denotes a water-soluble block that comprises a poly(ethylene glycol) (or poly(oxyethylene)) chain, and a polyanionic polymer.

1 Claim, 14 Drawing Sheets

[FIG. 1]
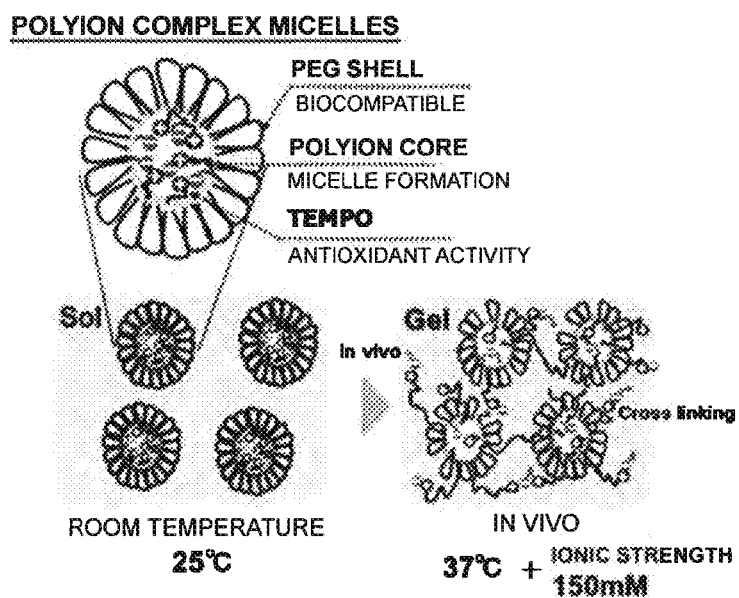
[FIG. 2]
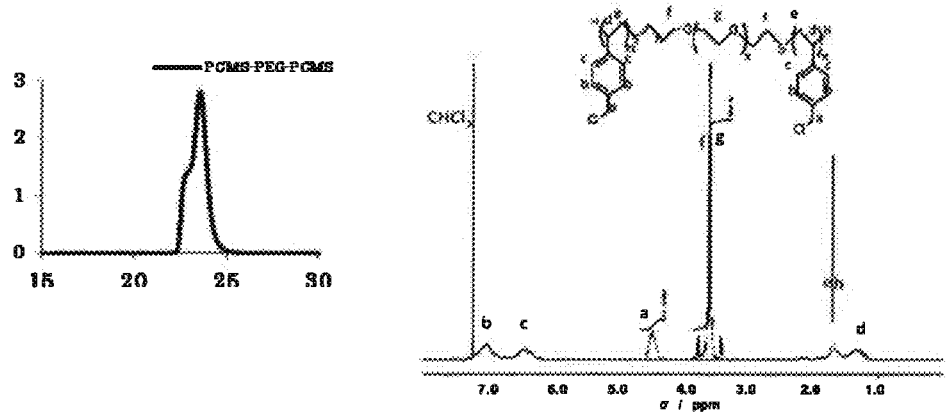

[FIG. 3]
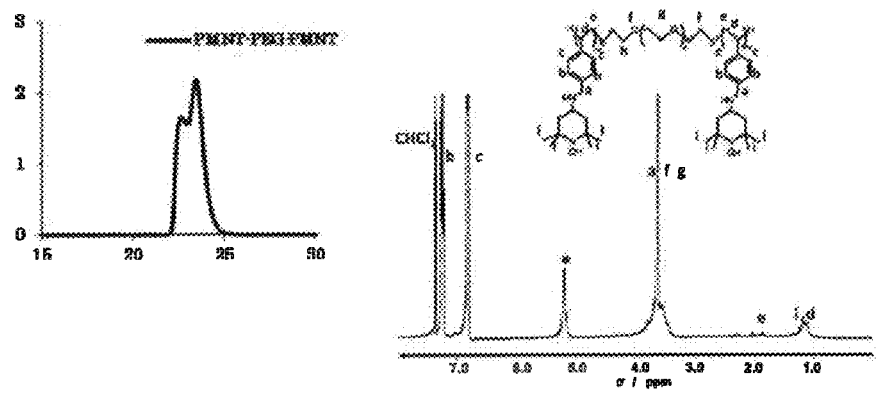
[FIG. 4]
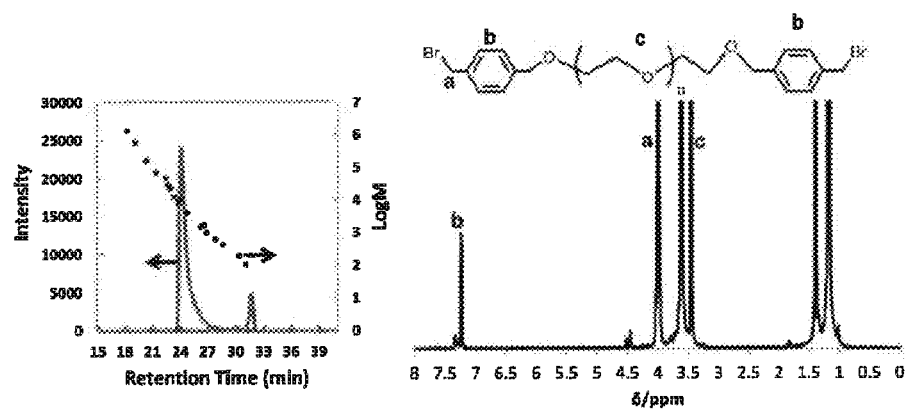
[FIG. 5]
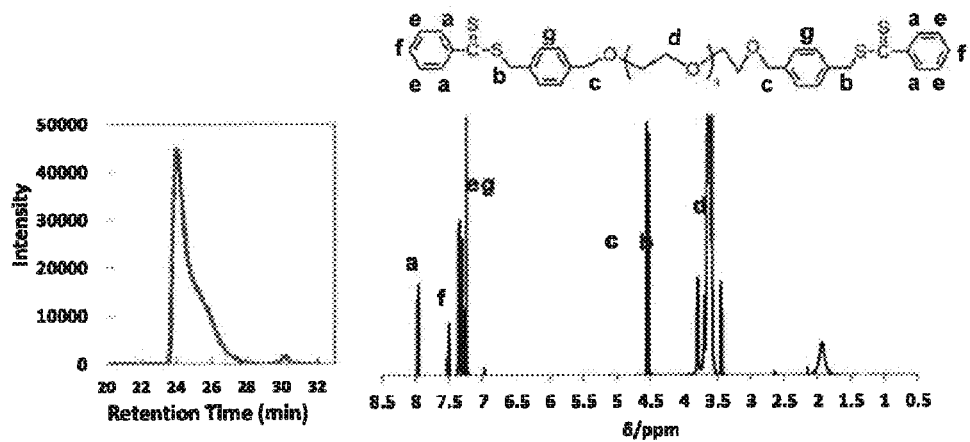

[FIG. 6]
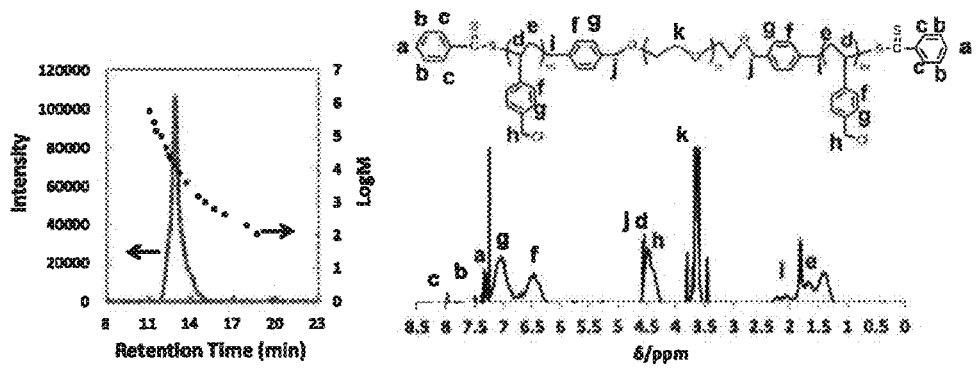
[FIG. 7]
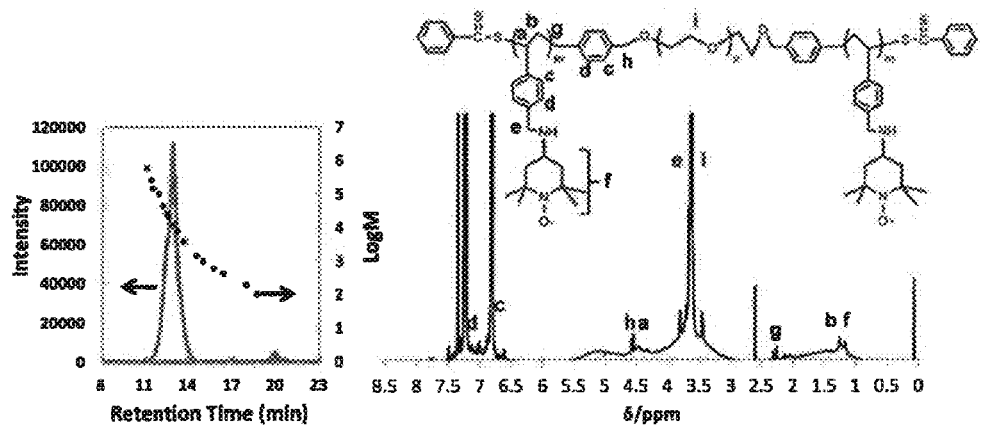
[FIG. 8]
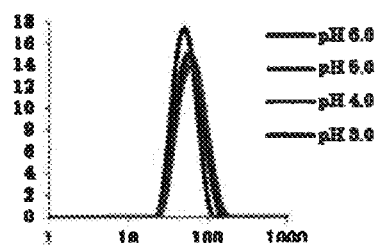

[FIG. 9]
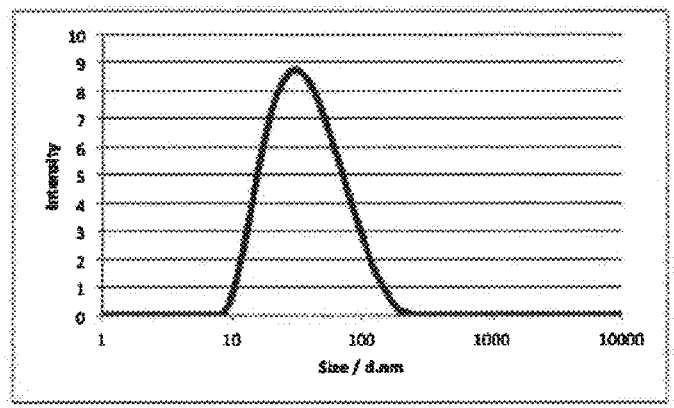
[FIG. 10]
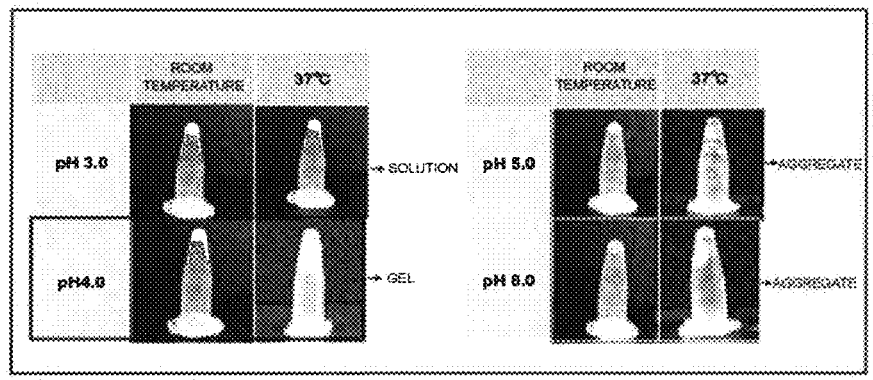
[FIG. 11]
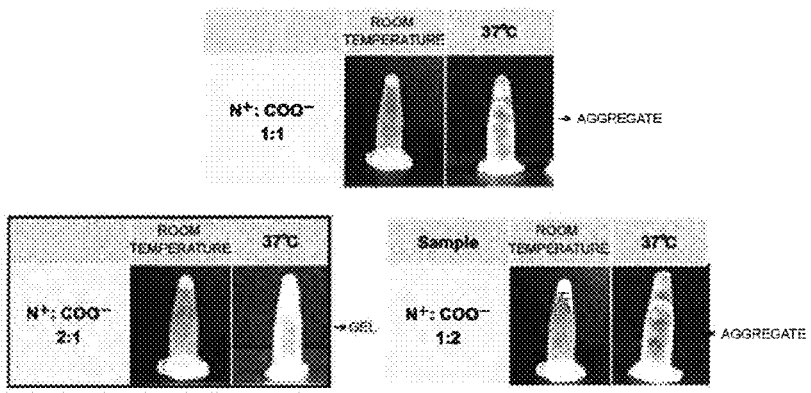

[FIG. 12]
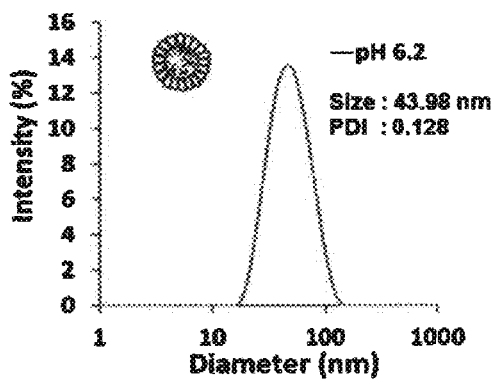
[FIG. 13]
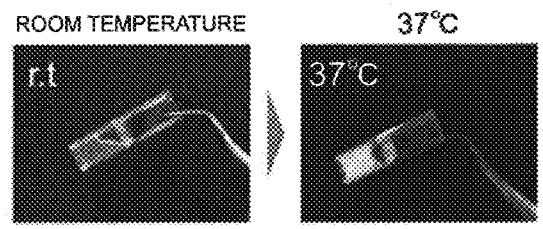
[FIG. 14]
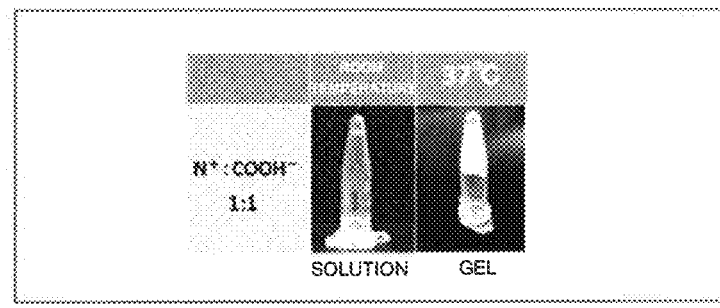

[FIG. 15]
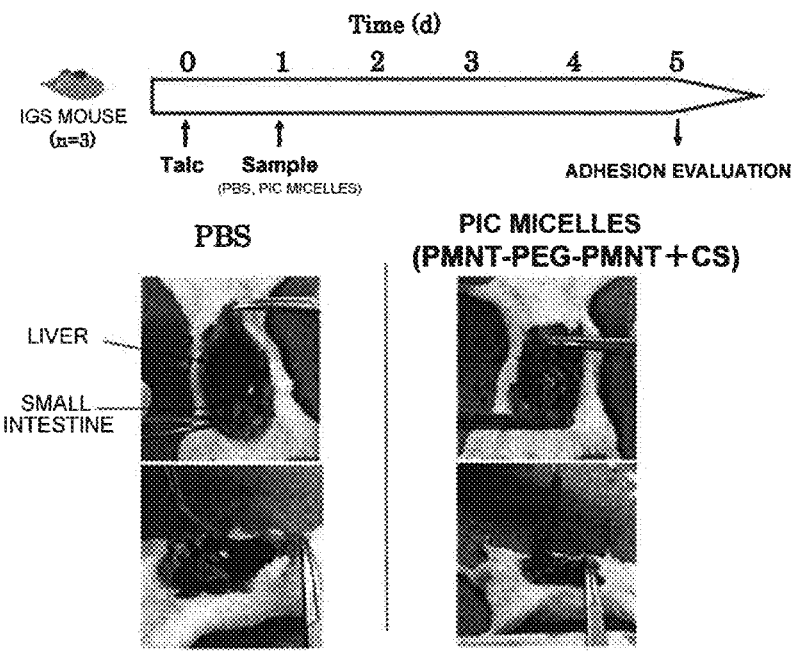
[FIG. 16]
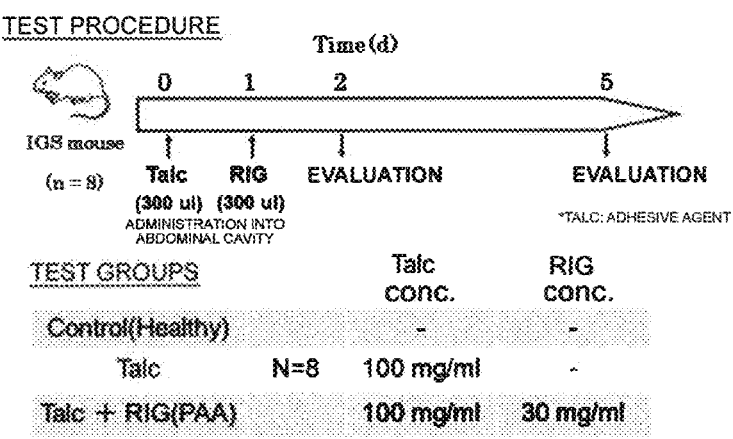

[FIG. 17]
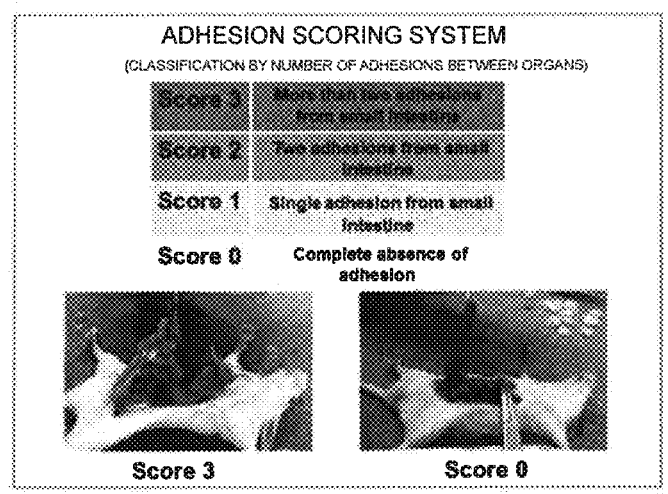
[FIG. 18]
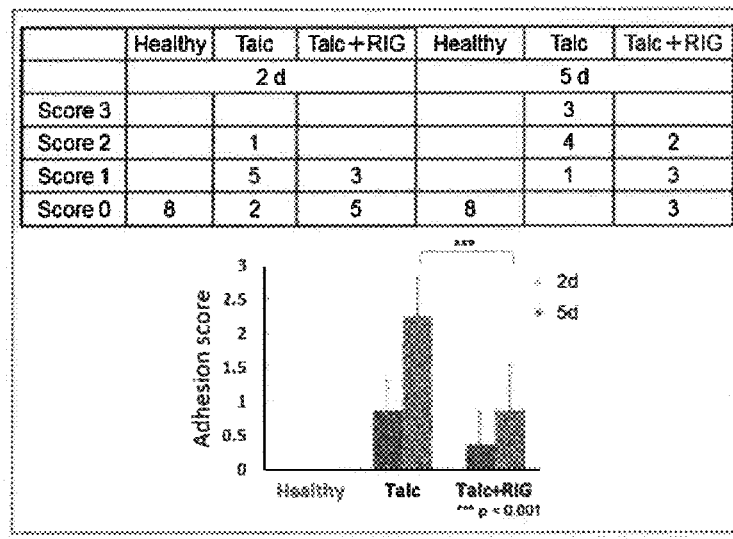

[FIG. 19]
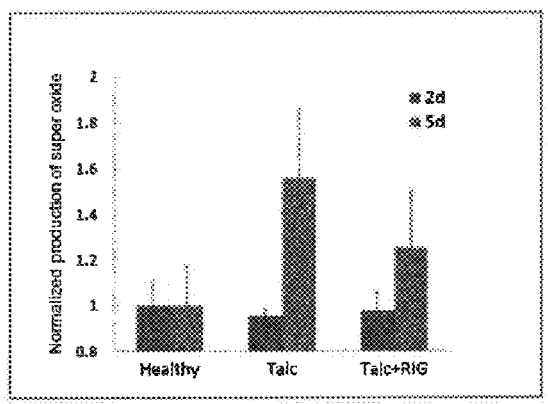
[FIG. 20]
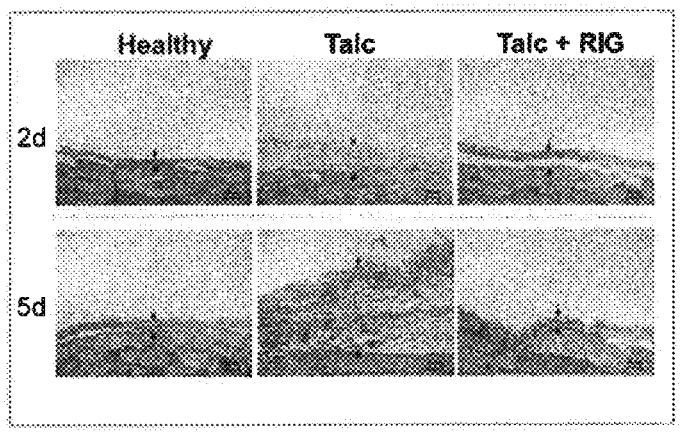
[FIG. 21]
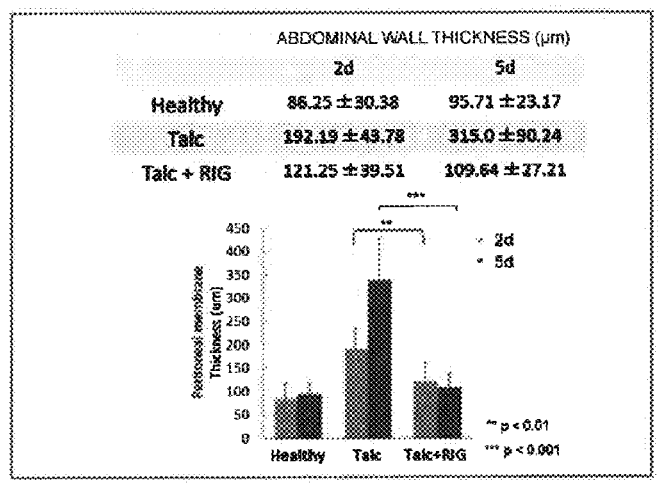

[FIG. 22]
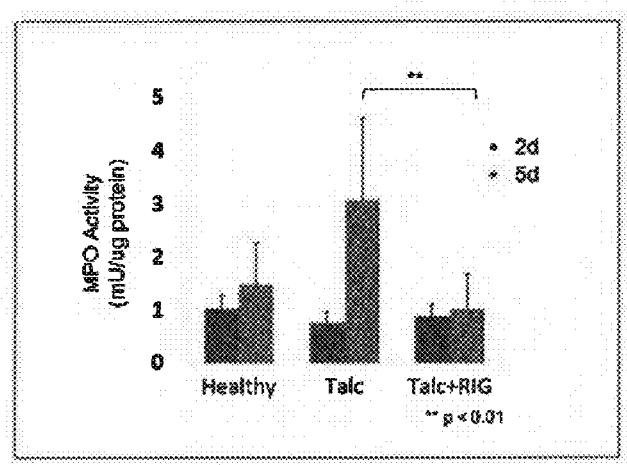
[FIG. 23]
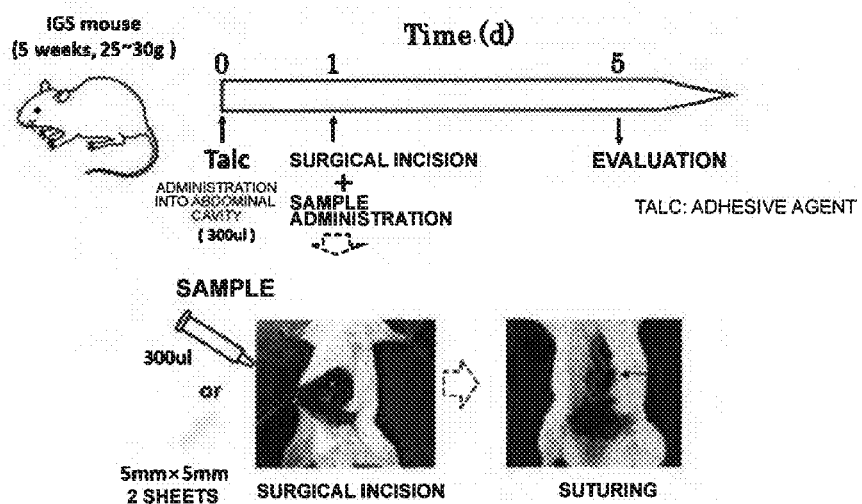

[FIG. 24]
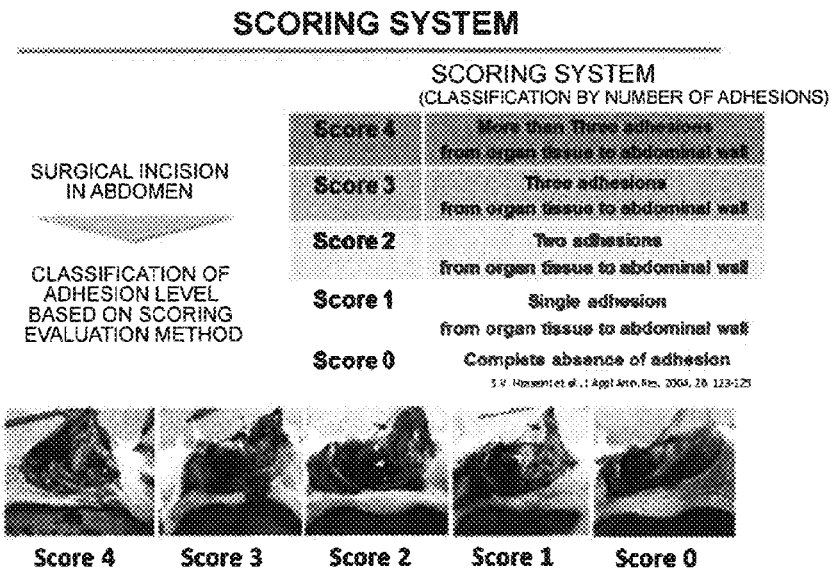
[FIG. 25]
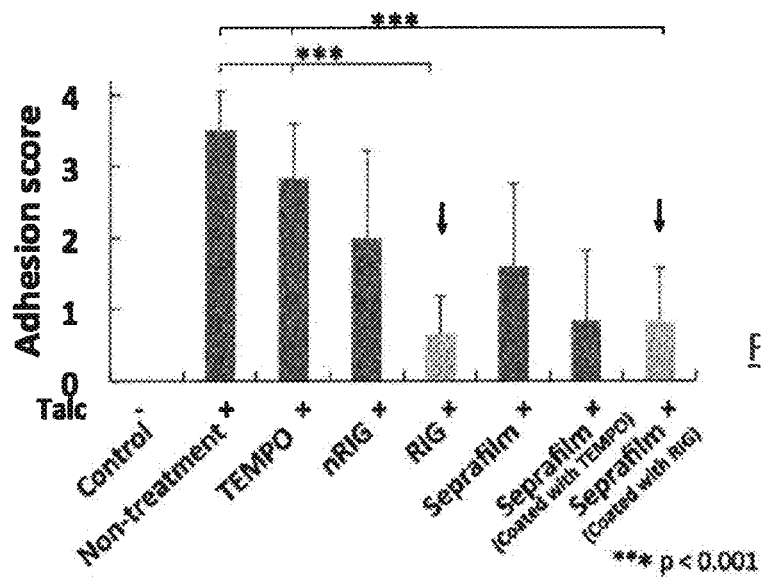

[FIG. 26]
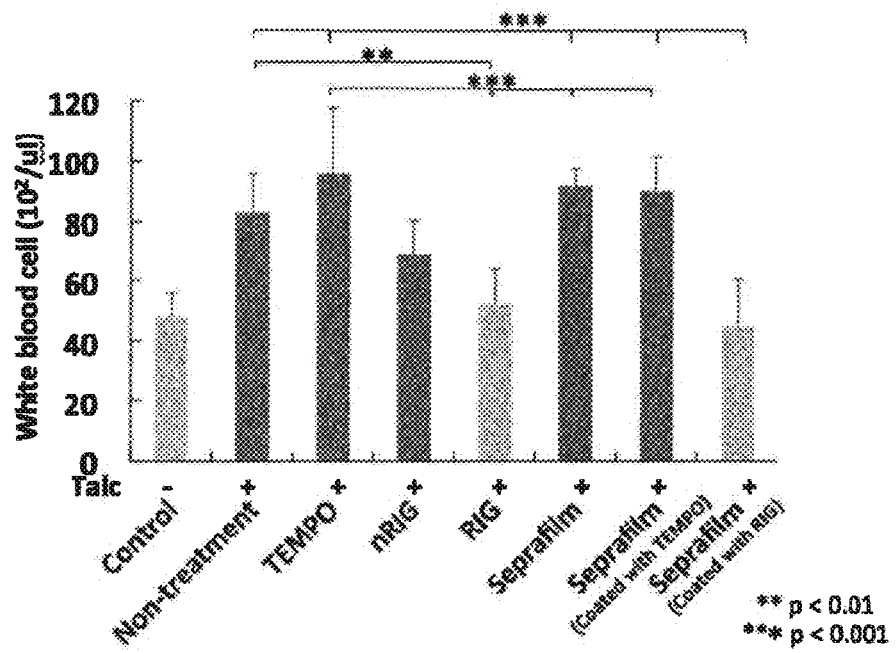
[FIG. 27]
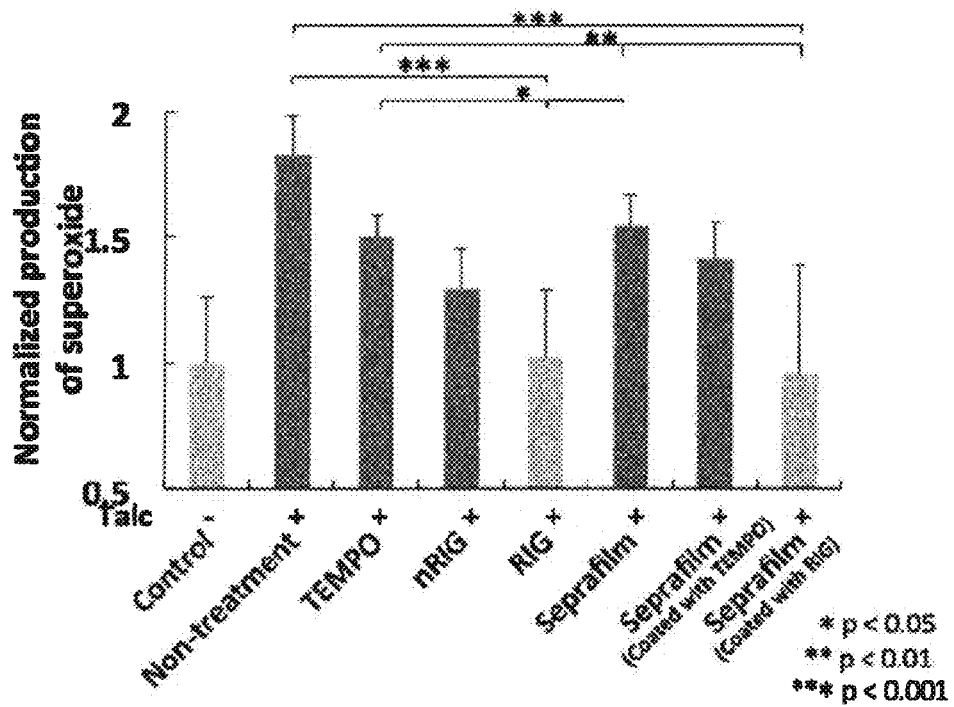

[FIG. 28]
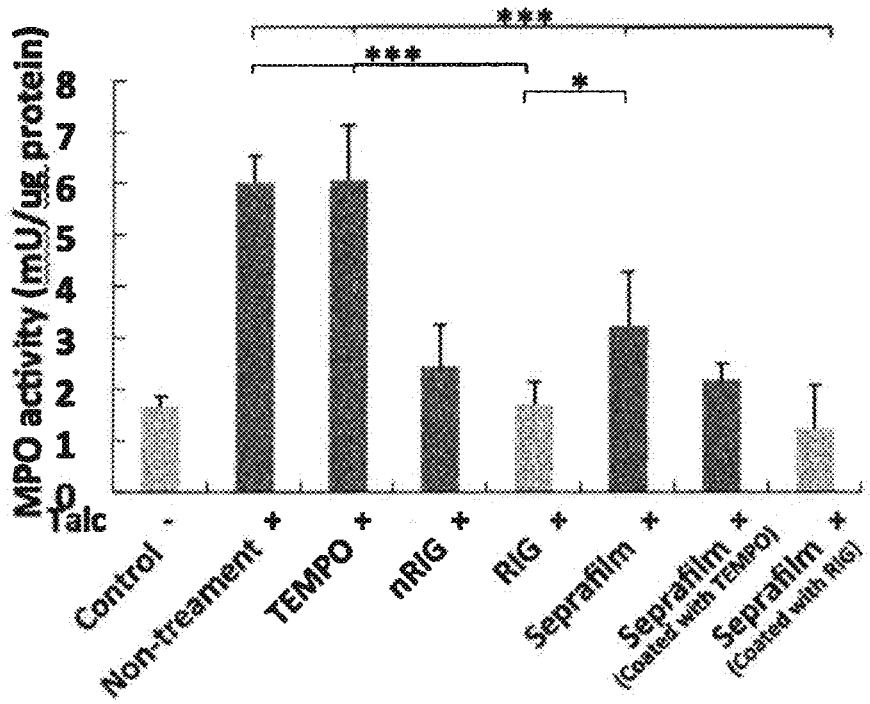
[FIG. 29]
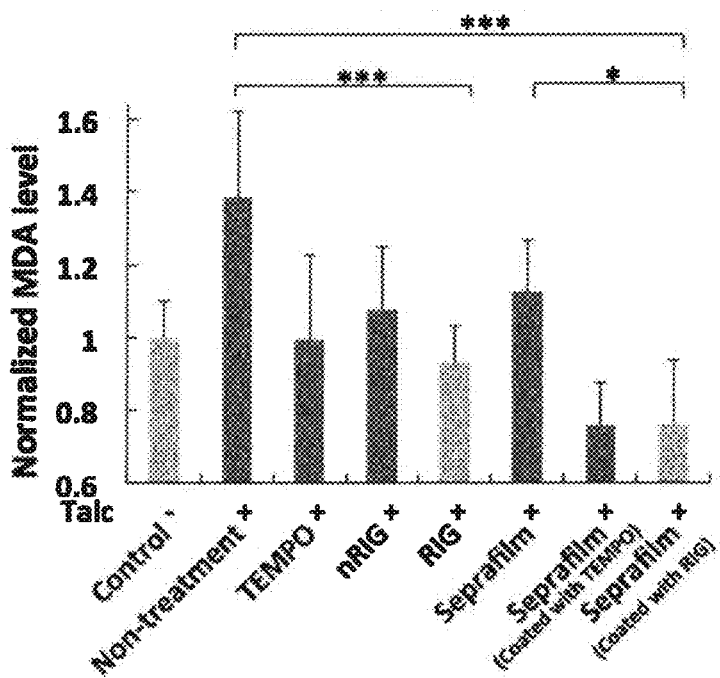

[FIG. 30]
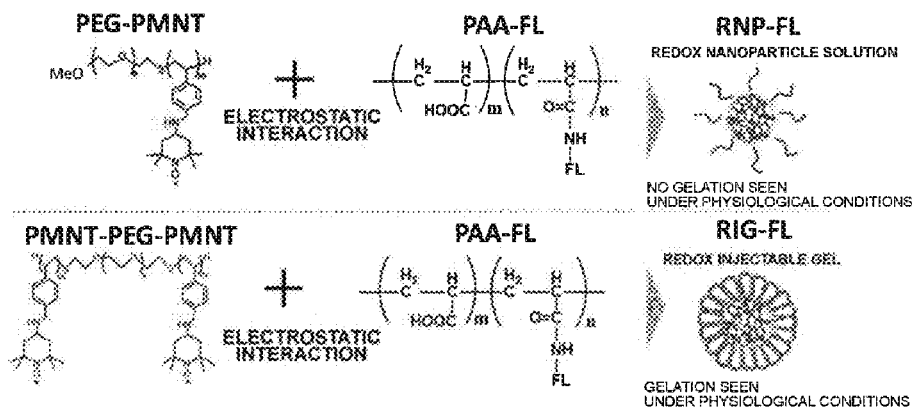
[FIG. 31]
[FIG. 32]
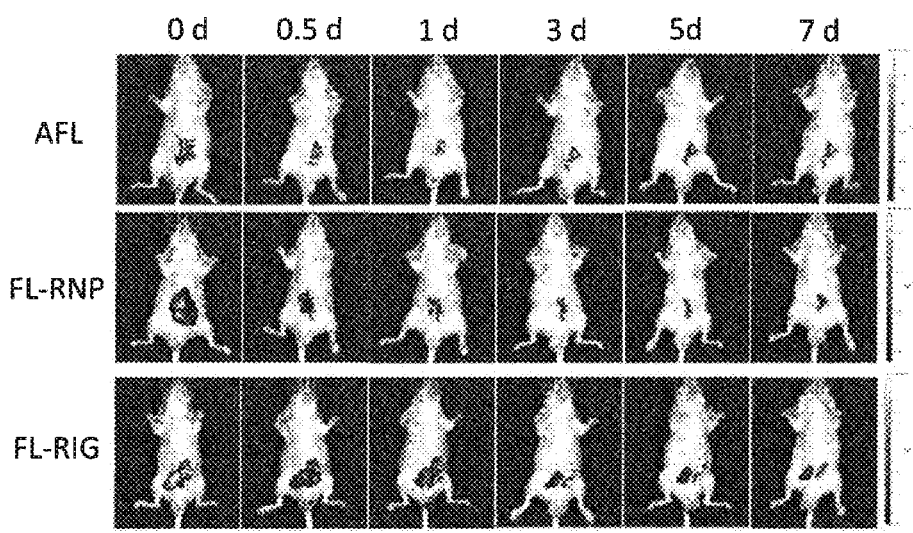

[FIG. 33]
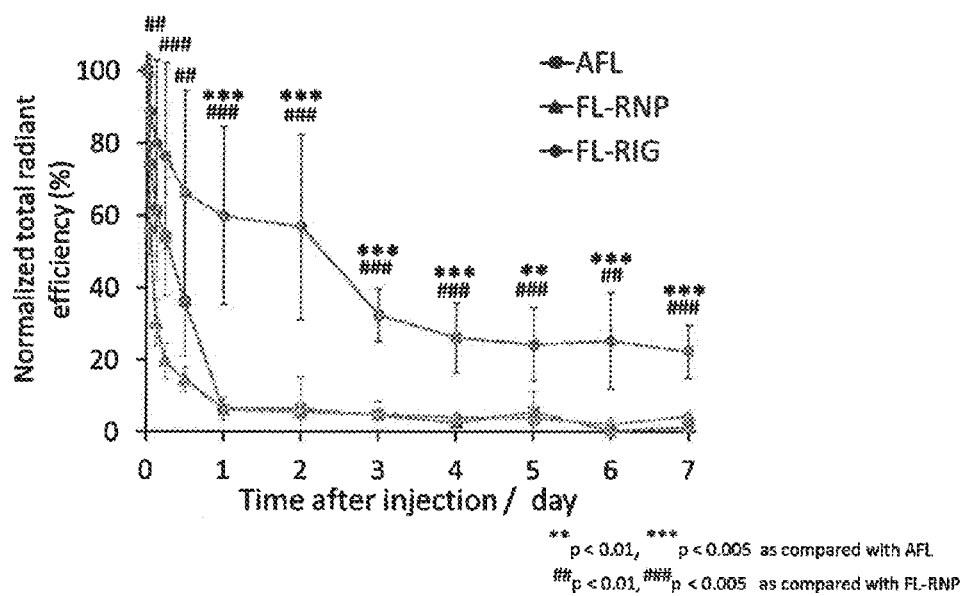

ADHESION-PREVENTING PREPARATION COMPRISING COMPOSITION COMPRISING POLYCATIONIC TRIBLOCK COPOLYMER AND POLYANIONIC POLYMER

TECHNICAL FIELD

The present invention relates to an adhesion-preventing preparation comprising, as an active ingredient, a composition comprising a polycationic triblock copolymer and a polyanionic polymer.

BACKGROUND ART

Film-type and sheet-type adhesion-preventing agents comprising biocompatible substances have come to be used in surgical procedures. In the prior art, films employing materials intended for such applications, such as collagen-based materials or gel compositions derived from hyaluronic acid and carboxymethyl cellulose, have been proposed (for example, see Patent Document 1 and Patent Document 2). However, problems have been pointed out, such as this type of film being difficult to handle during surgery and exhibiting low covering properties on the surface of tissues. Meanwhile, development of materials to be used directly in the form of gels has progressed, and use of a carboxymethyl cellulose derivative that enables the formation of a hydrogel having excellent viscoelasticity as a medical gel or adhesion-preventing material has been proposed (for example, see Patent Document 3). Development of some of these gel-like adhesion-preventing materials has already progressed with a view to commercialization. However, the need remains for a gel-like adhesion-preventing material (or agent) having more effective adhesion prevention performance.

PRIOR ART DOCUMENT

Patent Document

Patent Document 1: Japanese Patent Application Laid-Open No. 2003-19194
Patent Document 2: Japanese Patent Application Laid-Open No. H3-295561
Patent Document 3: WO 2009/078492

SUMMARY OF INVENTION

Technical Problem

The present inventors have succeeded in stabilizing a cyclic nitroxide radical by covalently bonding the cyclic nitroxide radical to a specific block copolymer, and also found that reactive oxygen species (ROS) could thus be effectively eliminated (see WO 2009/133647). Furthermore, the present inventors succeeded in providing a gel by which an ion complex, which is formed from an anionic polymer and a cationic polymer obtained by covalently bonding this type of cyclic nitroxide radical to a specific triblock copolymer, is retained in an area of a living body requiring elimination of reactive oxygen species, such as periodontal pockets and cancer lesions, and is able to suppress inflammation, and filed an application for the thus completed invention (see WO2013/111801).

Meanwhile, for the current application, the present inventors have found that an aqueous ion complex solution able to provide this type of gel forms an irreversible gel under physiological conditions or in a living body, functions as a physical barrier that prevents adhesion between tissues or organs in a living body, and exhibits an excellent adhesion prevention effect. In addition, the present inventors found that by using the ion complex in the form of micelles in an aqueous solution in particular, it is possible to form an irreversible gel rapidly after administration to a living body. Although the present invention is not restricted by any theory, it is understood that this type of excellent adhesion prevention effect is achieved as a result of excellent physical barrier properties brought about by the irreversible gel that can be rapidly formed and also as a result of suppression of inflammation that occurs between tissues or organs that have been damaged by surgery or the like and surrounding tissue or organs.

Therefore, provided as means for solving the problems mentioned above are an adhesion-preventing preparation comprising, as an active ingredient, a composition comprising a triblock copolymer represented by formula I below and the polyanionic polymer shown below, use of this composition to produce adhesion-preventing preparation for tissues or organs in a living body, and an adhesion prevention method comprising administering this composition to a site in a living body that requires administration, at a quantity that is effective for preventing adhesion.

[Chemical Formula 1]

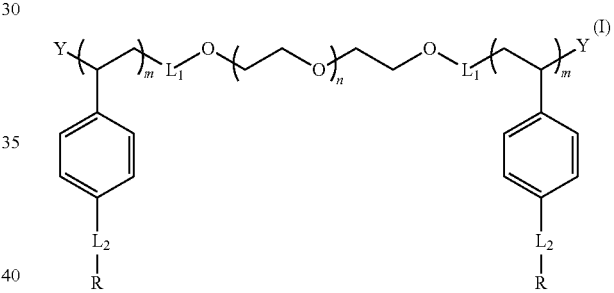

In the formula,
the $L_1$ groups are linking groups that may be the same as, or different from, each other,
the $L_2$ groups are each independently a —$C_{1-6}$ alkylene-NH—($C_{1-6}$ alkylene)$_q$— group, with q being an integer of 0 or 1,
the R groups are each independently such that at least 20% of the total number (n) of R groups are residues of cyclic nitroxide radical compounds selected from the group consisting of 2,2,6,6-tetramethylpiperidin-1-oxyl-4-yl groups, 2,2,5,5-tetramethylpyrrolidin-1-oxyl-3-yl groups, 2,2,5,5-tetramethylpyrrolin-1-oxyl-3-yl groups, 2,4,4-trimethyl-1,3-oxazolidin-3-oxyl-2-yl groups, 2,4,4-trimethyl-1,3-thiazolidin-3-oxyl-2-yl groups and 2,4,4-trimethyl-imidazolidin-3-oxyl-2-yl groups, with the remaining R groups, when present, being hydrogen atoms, halogen atoms or hydroxyl groups,
the Y groups are each independently selected from the group consisting of hydrogen, a phenylthiocarbonylthio group optionally substituted by a $C_{1-6}$ alkyl group, a $C_{1-6}$ alkylthiocarbonylthio group, a $C_{1-6}$ alkyloxythiocarbonylthio group, or SH
each instance of m is independently an integer between 3 and 1,000, and
n is an integer between 5 and 5,000.

Meanwhile, the anionic polymer is one or more types selected from the group consisting of a poly(acrylic acid), a poly(methacrylic acid), a poly(sulfonic acid), a polyanionic polysaccharide and an anionic protein.

Furthermore, the present invention relates to a composition in which 5 to 40% of carboxyl groups in the polyanionic polymer in the composition are modified by a fluorescent dye.

In addition, the present invention relates to a novel copolymer that is a part of the triblock copolymer represented by formula I, and a synthesis precursor thereof.

DESCRIPTION OF THE INVENTION

Unless defined otherwise, the technical terms used in the present specification have meanings and details that are commonly used in this technical field.

<Adhesion>

When surgery-damaged tissues or organs in normal living bodies are sutured, it is common for the tissues or organs to stick to each other and heal naturally (wound healing). However, tissues that should remain separated can stick together during the healing process, and this is called "post-operative adhesion", but in the present invention, adhesion broadly means a state whereby tissues, organs or tissue surfaces that should remain separated stick together due to trauma or inflammation, and includes this type of post-operative adhesion. Living body means that of a mammal, and of a human in particular, and patient means a mammal, and a human in particular.

<Triblock Copolymer>

The triblock copolymer represented by formula I is such that in the formula above,
the $L_1$ groups are preferably each independently selected from the group consisting of a single bond, —S—$(CH_2)_c$—, —S—$(CH_2)_c$CO—, —$(CH_2)_c$S— and —CO$(CH_2)_c$S—, and

[Chemical Formula 2]

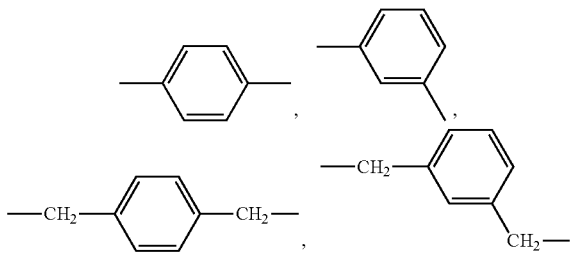

c is an integer between 1 and 5, and
Y is preferably hydrogen or a group selected from the group consisting of —SH and

[Chemical Formula 3]

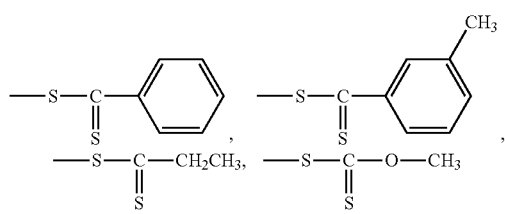

the R groups are preferably each independently such that generally 20%, preferably 50%, more preferably at least 80%, and most preferably approximately 90% or more or 100%, of the total number (n) of R groups are residues of cyclic nitroxide radical compounds selected from the group consisting of 2,2,6,6-tetramethylpiperidin-1-oxyl-4-yl groups, 2,2,5,5-tetramethylpyrrolidin-1-oxyl-3-yl groups, 2,2,5,5-tetramethylpyrrolin-1-oxyl-3-yl groups, 2,4,4-trimethyl-1,3-oxazolidin-3-oxyl-2-yl groups, 2,4,4-trimethyl-1,3-thiazolidin-3-oxyl-2-yl groups and 2,4,4-trimethyl-imidazolidin-3-oxyl-2-yl groups, with the remaining R groups, when present, being hydrogen atoms, halogen atoms or hydroxyl groups, each instance of m is independently an integer that is preferably between 3 and 100, and more preferably between 3 and 50 and n is an integer that is preferably between 5 and 1000, and more preferably between 10 and 200.

Moreover, in cases where bonding sites such as —S—$(CH_2)_c$—, which is given as an example of the linking group $L_1$ in formula I, are different, bonding to an oxygen atom (O) in the formula occurs via the linker on the right hand side in the direction shown in the formula (a linker represented by $(CH_2)_c$— in this example), and $L_2$ bonds to R via a NH—$(C_{1-6}$ alkylene$)_q$— linker.

In the present invention, $C_{1-6}$ alkyl groups or groups including $C_{1-6}$ alkyl groups, such as alkyl moieties in $C_{1-6}$ alkylthiocarbonylthio groups and $C_{1-6}$ alkyloxythiocarbonylthio groups, are not limited, but specific examples thereof include branched chain or straight chain lower alkyl groups such as methyl groups, ethyl groups, n-propyl groups, iso-propyl groups, n-butyl groups, sec-butyl groups, tert-butyl groups and hexyl groups.

The $C_{1-6}$ alkylene group is not limited, and specific examples thereof include diyl groups of corresponding alkyl groups, such as methylene groups, 1,2-propanediyl groups, 1,3-propanediyl groups and 1,4-butanediyl groups.

The cyclic nitroxide radical of the R group is preferably a group represented by
the following formulae:

[Chemical Formula 4]

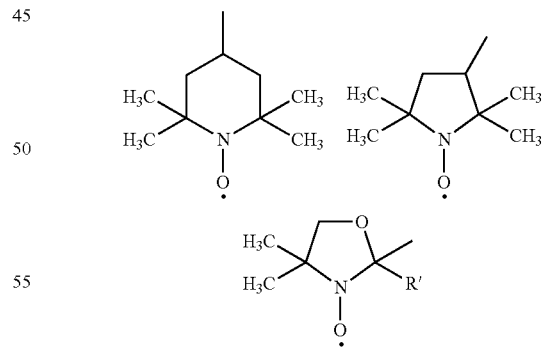

in the formulae, R' is a methyl group.

This type of triblock copolymer is disclosed in WO 2013/111801, and the contents disclosed in that document are incorporated by reference in the contents of the present specification. In addition, a product that cannot be produced using the method disclosed in the pamphlet of that international publication can be efficiently produced using the method described below.

<Polyanionic Polymer>

The polyanionic polymer used in the present invention is a polyanionic organic polymer compound able to form a stable polyion complex with the triblock copolymer represented by formula I in an aqueous solution. Specific examples thereof are not limited, but include one or more types selected from the group consisting of a poly(acrylic acid), a poly(methacrylic acid), a poly(sulfonic acid), a polyanionic polysaccharide and an anionic protein, with preferred examples including polyanionic polysaccharides selected from the group consisting of carboxymethyl dextran, carrageenan, xanthan gum, chondroitin sulfate, hyaluronic acid and heparin; and anionic proteins selected from the group consisting of albumin, poly(aspartic acid) and poly(glutamic acid). Anionic polysaccharides are particularly preferred. Optimal values for the molecular weights of these polyanionic polymers vary according to the type of polymer, but are not limited. However, in the case of a poly(acrylic acid), the Mn value is 1,000 to 1,000,000, preferably 1,000 to 100,000, and more preferably 1,000 to 10,000, in the case of a polyanionic polysaccharide such as chondroitin sulfate, the Mn or Mw value is 1,000 to 1,000,000, and preferably 1,000 to 100,000, and in the case of an anionic protein such as a poly(aspartic acid), the Mn or Mw is 1,000 to 1,000,000, and preferably 1,000 to 100,000. These polyanionic polymers can be commercially available products, refined if necessary.

In addition, modified anionic polymer means a compound that is modified as a result of a carboxylic acid group in a polyanionic polymer mentioned above, such as a poly(acrylic acid), a poly(methacrylic acid), carboxymethyl dextran, xanthan gum, hyaluronic acid, poly(aspartic acid) or poly(glutamic acid), covalently bonding to a functional group able to covalently bond to a carboxyl group in a fluorescent dye, such as a fluorescein dye, a rhodamine dye or an Alexa Fluor dye.

<Mode of Use of Triblock Copolymer and Polyanionic Polymer or Modified Anionic Polymer>

It is preferable for the triblock copolymer and the polyanionic polymer or modified anionic polymer to be used at proportions whereby transparent polyion complex micelles can be present due to a composition comprising the triblock copolymer and the polyanionic polymer or modified anionic polymer forming micelles by molecules of the triblock copolymer and the polyanionic polymer or modified anionic polymer associating in an ordinary aqueous solution (for example, a solution obtained by a solute dissolving or dispersing in pure water or ion exchanged water). In order to simplify understanding of the present invention, a conceptual diagram of such ion complex micelles is shown in FIG. 1. In order to be more consistent with the objective of the present invention, this type of micelle solution must comprise the triblock copolymer and the polyanionic polymer or modified anionic polymer at proportions such that it allows the formation of an irreversible gel by virtue of changes in ionic strength, pH, temperature, etc. of the aqueous solution, and especially by virtue of a change in the prepared micelle solution accompanying a change from being in vitro at room temperature to being in an in vivo environment or under physiological conditions. Such changes mean, for example, the ionic strength changing from an ion concentration of 0 or several tens of mM to an ion concentration of 150 mM, or temperature changes such as an increase to approximately 37° C. or higher (whereas the micelles are generally formed at room temperature). Therefore, a composition provided by the present invention exhibits in vivo retention, but can also effectively prevent adhesion of tissues or organs, which is caused by inflammation, as a result of a cyclic nitroxide radical compound supported by the triblock copolymer being able to eliminate reactive oxygen species. In addition, a composition comprising the triblock copolymer and the modified anionic polymer exhibits this in vivo retention and enables in vivo behavior of the composition (the polyion complex) to be detected by means of a modifying group or moiety. It is possible to use IVIS imaging as this type of detection.

These proportions are such that the ratio of the number of moles of amino groups (or imino groups) in the triblock copolymer and the number of moles of anionic groups in the polyanionic polymer or modified anionic polymer is 1:4 to 4:1, preferably 1:1 to 4:1, and more preferably such that the number of moles of the former exceeds the number of moles of the latter.

The polyion complex formed from the composition may, if necessary, be provided as an aqueous polyion complex micelle solution that comprises a physiologically acceptable diluent or excipient. This type of diluent can be sterilized water, a mineral acid-containing acidic aqueous solution, a physiological saline solution, a solution containing a physiologically acceptable buffering agent, or the like, and the excipient can be, for example, sorbitol, dextrin, glucose, mannitol, an amino acid (for example, glycine, isoleucine, valine, methionine, glutamic acid), or the like. The effective quantity of a preparation prepared in this way can be easily decided by a specialist doctor on the basis of results of efficacy tests and the like performed using laboratory animals, such as those mentioned below.

In the present invention, the composition is applied or administered to a site in a living body in which adhesion of tissue or organs must be prevented or suppressed, if necessary after sterilizing the polyion complex, and especially the micelle solution, by means of a sterilization method that is publicly known in this technical field, electron beam irradiation, or the like. Because this type of application enables injection using an appropriate type of injection tool, such as an injector, there are no limits when selecting a specific target site.

<Novel Triblock Copolymer>

A triblock copolymer in which, in formula I, the $L_1$ groups are each independently selected from the group consisting of

[Chemical Formula 5]

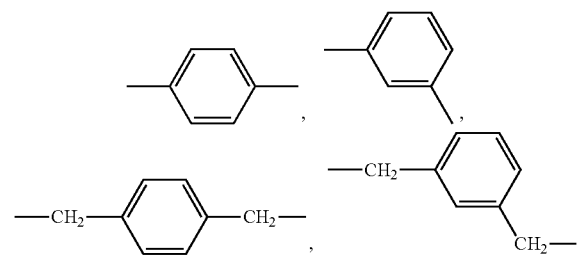

the Y groups are each independently selected from the group consisting of hydrogen, a phenylthiocarbonylthio group optionally substituted by a $C_{1-6}$ alkyl group, a $C_{1-6}$ alkylthiocarbonylthio group, a $C_{1-6}$ alkyloxythiocarbonylthio group, or SH, that is, a triblock copolymer represented by formula II below,

[Chemical Formula 6]

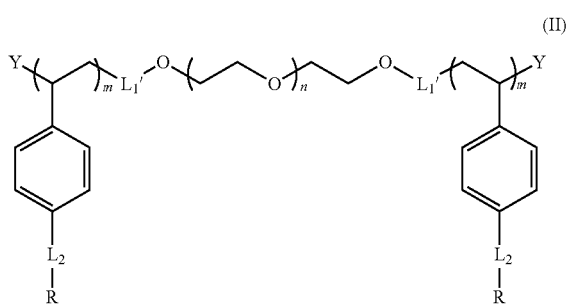

in the formula, the $L_1'$ groups are each independently selected from the group consisting of

[Chemical Formula 7]

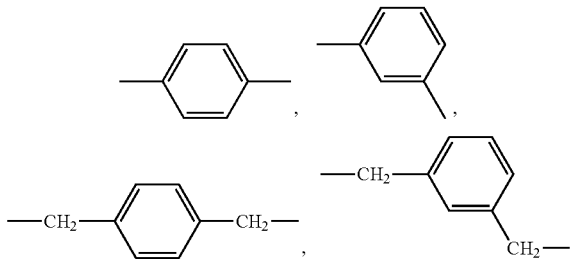

the Y groups are each independently selected from the group consisting of hydrogen, a phenylthiocarbonylthio group optionally substituted by a $C_{1-6}$ alkyl group, a $C_{1-6}$ alkylthiocarbonylthio group, a $C_{1-6}$ alkyloxythiocarbonylthio group, or SH and $L_2$, R, m and n are as defined above in relation to formula I, is not disclosed in WO 2013/111801 and is, as far as the present inventors are aware, a novel compound that is not disclosed in prior art documents.

This type of triblock copolymer can be provided by, for example, polymerizing chloromethylstyrene with a both terminal-modified poly(ethylene glycol) or poly(oxyethylene) derivative represented by formula a below

[Chemical Formula 8]

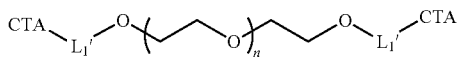

in the formula, $L_1'$ and n are as defined above in relation to formula II, CTA is a chain transfer agent selected from, for example, the group consisting of a phenylthiocarbonylthio group optionally substituted by a $C_{1-6}$ alkyl group, a $C_{1-6}$ alkylthiocarbonylthio group or a $C_{1-6}$ alkyloxythiocarbonylthio group, for 18 to 24 hours at a temperature of 20° C. to 80° C. in an inert solvent such as toluene in the presence of an azo compound, such as 2,2'-azobisisobutyronitrile (AIBN), as a radical source

[Chemical Formula 9]

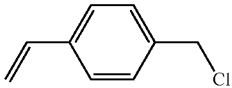

so as to obtain a triblock copolymer precursor represented by formula b below

[Chemical Formula 10]

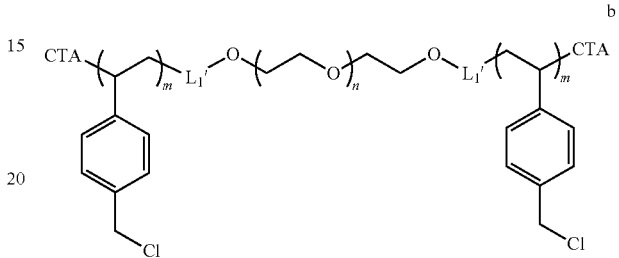

in the formula, CTA, $L_1'$, m and n are as defined above, and then reacting with an amine represented by

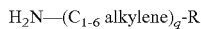

in the formula, R is as defined above in relation to formula I for 3 to 72 hours at a temperature between room temperature and 70° C. in a solvent such as dimethylformamide in the presence, if necessary, of a dehydrohalogenation agent such as pyridine and then, if necessary, treating under reducing conditions.

These methods are advantageous in terms of being suitable for commercial scale production due to having lower production costs than the triblock copolymer production method disclosed in WO 2013/111801, and also in terms of being able to effectively control the molecular weight and polydispersity of the polymer per se.

Therefore, the present invention relates to a triblock copolymer for producing the composition of the present invention, a precursor of this triblock copolymer, and a method for producing this triblock copolymer.

BRIEF DESCRIPTION OF DRAWINGS

FIG. 1 is a conceptual diagram of ion complex micelles according to the present invention.

FIG. 2 is a diagram showing the results of size exclusion chromatography (SEC) measurements and $^1$H NMR spectral measurements for the PCMS-b-PEG-b-PCMS triblock copolymer obtained in Production Example 1.

FIG. 3 is a diagram showing the results of SEC measurements and $^1$H NMR spectral measurements for the PMNT-b-PEG-b-PMNT triblock copolymer obtained in Production Example 1.

FIG. 4 is a diagram showing the results of SEC measurements and $^1$H NMR spectral measurements for the Br-PEG-Br polymer obtained in Production Example 2.

FIG. 5 is a diagram showing the results of SEC measurements and $^1$H NMR spectral measurements for the CTA-PEG-CTA polymer obtained in Production Example 2.

FIG. 6 is a diagram showing the results of SEC measurements and $^1$H NMR spectral measurements for the PCMS-PEG-PCMS triblock copolymer obtained in Production Example 2.

FIG. 7 is a diagram showing the results of SEC measurements and ¹H NMR spectral measurements for the PMNT-PEG-PMNT triblock copolymer obtained in Production Example 2.

FIG. 8 is a diagram showing particle size distributions of polyion complex micelles (PMNT-PEG-PMNT+CS) prepared in Production Example 1. The vertical axis shows intensity (%), and the horizontal axis shows particle size.

FIG. 9 is a diagram showing the particle size distribution of the polyion complex micelles prepared in Production Example 2. The vertical axis shows intensity (%), and the horizontal axis shows particle size.

FIG. 10 shows photographs in place of drawings that show the state of gelation in Production Example 1 (1).

FIG. 11 shows photographs in place of drawings that show the state of gelation in Production Example 1 (2).

FIG. 12 is a diagram showing the particle size distribution of polyion complex micelles (PMNT-PEG-PMNT+PAA) prepared in Production Example 1. The vertical axis shows intensity (%), and the horizontal axis shows particle size.

FIG. 13 shows photographs in place of drawings that show the state of gelation of polyion complex micelles (PMNT-PEG-PMNT+PAA) prepared in Production Example 1.

FIG. 14 shows photographs in lieu of drawings that show the state of gelation of the polyion complex micelles (PMNT-PEG-PMNT+PAA) prepared in Production Example 1.

FIG. 15 shows photographs that show the adhesion prevention effect of polyion complex micelles (PMNT-PEG-PMNT+CS) prepared in Production Example 1.

FIG. 16 is a diagram that shows the experimental procedure used when carrying out Test 2.

FIG. 17 is a diagram relating to the adhesion scoring system used in Test 2.

FIG. 18 is a diagram showing quantitative evaluation of adhesion levels by means of a scoring system in Test 2.

FIG. 19 is a diagram showing evaluation of reactive oxygen species production in abdominal wall segments in Test 2.

FIG. 20 shows diagrams of histological examinations of abdominal wall segments in Test 2.

FIG. 21 is a diagram showing abdominal wall thickness measurement results for abdominal wall segments in Test 2.

FIG. 22 is a diagram showing MPO activity evaluations in Test 2.

FIG. 23 is a diagram that relates to the experimental procedure used when carrying out Test 3.

FIG. 24 is a diagram relating to the adhesion scoring system used in Test 3.

FIG. 25 is a diagram showing quantitative evaluation of adhesion levels by means of a scoring system in Test 3.

FIG. 26 is a diagram showing the number of white blood cells in blood in Test 3.

FIG. 27 is a diagram showing evaluation of reactive oxygen species production in abdominal wall segments in Test 3.

FIG. 28 is a diagram showing MPO activity evaluations of abdominal wall segments in Test 3.

FIG. 29 is a diagram showing evaluation of degree of lipid peroxidation in Test 3.

FIG. 30 is a conceptual diagram relating to Production Example 3 (2) and gelation.

FIG. 31 shows photographs in place of diagrams that show the results of an ion complex gelation test in Production Example 3 (2).

FIG. 32 shows photographs in place of drawings that show the results of imaging of samples in Test 4.

FIG. 33 is a graph showing quantitative data that indicates residual quantities of samples in Test 4.

WORKING EXAMPLES

The present invention will now be explained in greater detail through the use of specific examples, but is in no way limited to these specific examples.

A. Polychloromethylstyrene-b-Poly(Ethylene Glycol)-b-Polychloromethylstyrene Triblock Copolymer, Cyclic Nitroxide Radical-Modified Compound Thereof, (Ion Complex of) this Modified Compound and Polyanionic Polymer, and Use Thereof Production Example 1

(1) Synthesis of polychloromethylstyrene-b-poly(ethylene glycoD-b-polychloromethylstyrene (PCMS-b-PEG-b-PCMS) Triblock Copolymer The PCMS-b-PEG-b-PCMS was synthesized according to Synthesis Scheme 1 shown below:

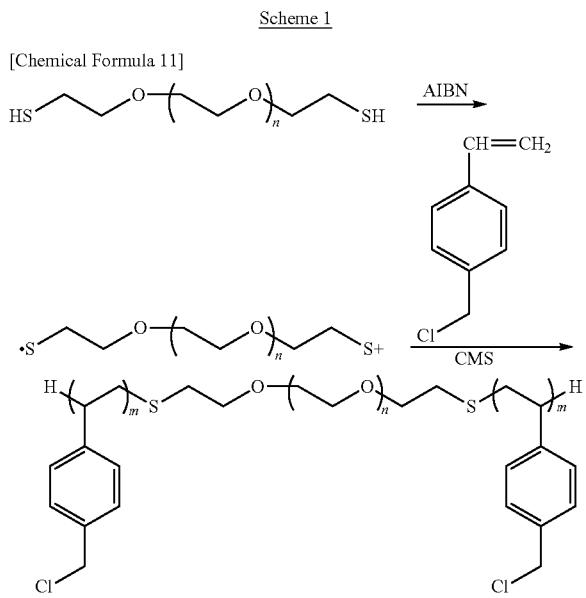

Scheme 1

[Chemical Formula 11]

Poly(ethylene glycol) having a thiol group at both terminals (HS-PEG-SH) (Mn: 10,000; 0.107 mmol, 1.07 g) was added to a reaction vessel. Next, a procedure involving evacuating the reaction vessel to a vacuum and blowing in nitrogen gas was repeated 3 times so as to form a nitrogen atmosphere in the reaction vessel. A solution of 2,2'-azobisisobutyronitrile/toluene (0.107 mmol/10 ml) and a solution of chloromethylstyrene (8.03 mmol, 1.13 ml) were added to the reaction vessel, heated to 60° C. and stirred for 24 hours. A white powder was obtained by washing the reaction mixture 3 times with diethyl ether, which is a good solvent for a polychloroethylstyrene homopolymer, and then freeze-drying in benzene. The quantity recovered was 1.28 mg, which was a yield of 90.3%. The results of size exclusion chromatography (SEC) measurements and ¹H NMR spectral measurements for the obtained PCMS-b-PEG-b-PCMS triblock copolymer are shown in FIG. 2.

(2) Synthesis of Triblock Polymer Containing 2,2,6,6-tetramethylpiperidin-1-oxyl-4-yl (TEMPO) (PMNT-b-PEG-b-PMNT)

The PCMS-b-PEG-b-PCMS obtained in (1) above (Mn: 13,263; 1.12 g, 0.084 mmol) was added to the reaction vessel. Next, 4-amino-TEMPO (1.545 g, 0.422 mmol) was dissolved in 20 ml of dimethyl sulfoxide (DMSO), added to the reaction vessel, and stirred for 24 hours at room temperature. Following completion of the reaction, the reaction solution was added to a dialysis membrane (Spectra/Por molecular weight cut-off size 3,500, Spectrum Medical Industries Inc., Houston Tex.), and dialyzed with 2 L of methanol. The methanol was replaced 8 times at intervals of 2 hours, after which the reaction solution was subjected to evaporation and freeze-dried in benzene. The yield was 90.1%. It was found from $^1$H NMR measurements that 100% of the chloromethyl groups had reacted and TEMPO had been introduced (see FIG. 3).

Production Example 2

(1) Synthesis of Br-PEG (poly(ethylene glycol))-Br

The Br-PEG-Br was synthesized according to Synthesis Scheme 2 shown below:

Scheme 2

[Chemical Formula 12]

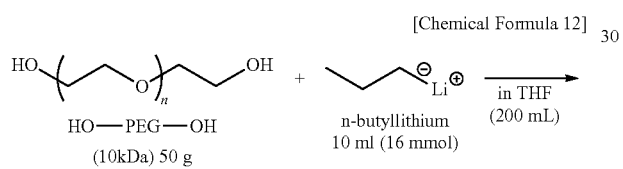

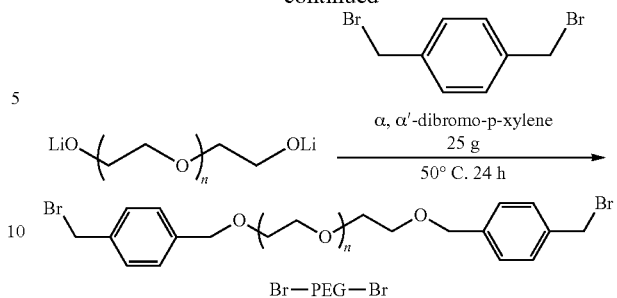

A poly(ethylene glycol) having a hydroxyl group at both terminals (HO-PEG-OH) (Mn: 10,000; 50 g) was dehydrated by means of vacuum drying at 110° C. for 12 hours. Next, 200 ml of tetrahydrofuran (THF) was added, 10 ml (16 mmol) of butyl lithium and 25 g of dibromoxylene were added thereto, and a reaction was allowed to progress at 50° C. for 24 hours, thereby obtaining Br-PEG-Br, which was brominated at both terminals. The obtained polymer was purified by being precipitated in 2-propanol and vacuum dried. The results of size exclusion chromatography (SEC) measurements and $^1$H NMR spectral measurements for the obtained Br-PEG-Br are shown in FIG. 4.

(2) Synthesis of CTA (Chain Transfer Agent)-PEG-CTA (Chain Transfer Agent) (Synthesis of PEG Having a Dithiophenyl Ester at Both Terminals)

The CTA-PEG-CTA was synthesized according to Synthesis Scheme 3 shown below:

Scheme 3

[Chemical Formula 13]

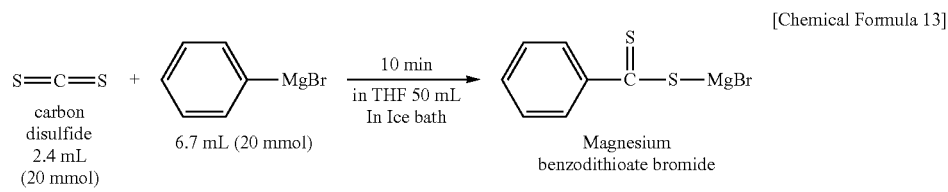

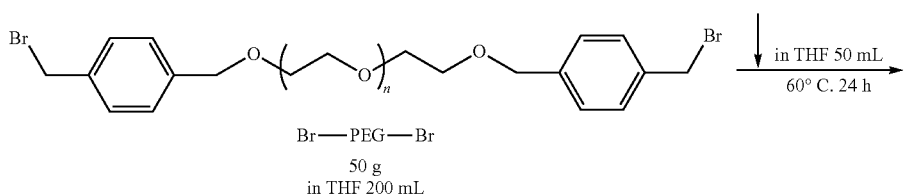

Chain Transfer Agent-PEG-Chain Transfer Agent (CTA—PEG—CTA)

2.4 ml of carbon disulfide was added to 50 ml of THF. Next, magnesium benzothiobromide was obtained by gradually adding 6.7 ml (20 mmol) of benzyl magnesium bromide under ice cooling and allowing a reaction to progress. The target CTA (Chain Transfer Agent)-PEG-CTA (Chain Transfer Agent) was obtained by dissolving 50 g of the Br-PEG-Br synthesized in Production Example 2 (1) in 200 ml of THF, adding the entire quantity of the prepared magnesium benzothiobromide, and allowing a reaction to progress at 60° C. for 24 hours. The obtained CTA-PEG-CTA was purified by being precipitated in 2-propanol and vacuum dried. The results of size exclusion chromatography (SEC) measurements and $^1$H NMR spectral measurements for the obtained polymer are shown in FIG. 5.

(3) Synthesis of polychloromethylatyrene-b-poly (ethylene glycol)-b-polychloromethylstyrene (PCMS-b-PEG-b-PCMS) triblock copolymer The PCMS-b-PEG-b-PCMS was synthesized according to Synthesis Scheme 4 shown below:

Scheme 4

[Chemical Formula 14]

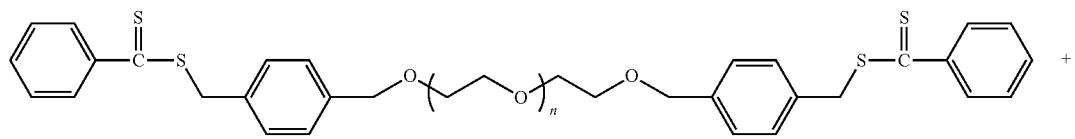

PEG—CTA 10 g

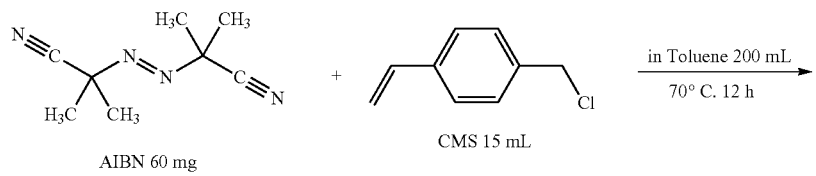

AIBN 60 mg     CMS 15 mL in Toluene 200 mL
70° C. 12 h

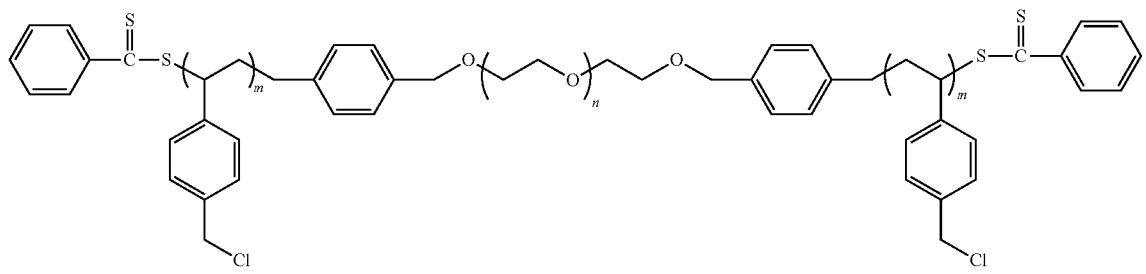

PCMS—PEG—PCMS

The target PCMS-b-PEG-b-PCMS was obtained by adding 10 g of the CTA-PEG-CTA synthesized in Production Example 2 (2), 60 mg of azobisisobutyronitrile (AIBN) to 200 ml of toluene in a nitrogen atmosphere, adding 15 ml of chloromethylstyrene (CMS) and stirring at 60° C. for 24 hours. The obtained polymer was purified by being precipitated in 2-propanol and vacuum dried. The results of size exclusion chromatography (SEC) measurements and ¹H NMR spectral measurements for the obtained PCMS-b-PEG-b-PCMS are shown in FIG. 6.

(4) Synthesis of Triblock Copolymer Containing 2,2,6,6-tetramethylpiperidin-1-oxyl-4-yl (TEMPO) (PMNT-b-PEG-b-PMNT)

A PMNT-b-PEG-b-PMNT triblock copolymer was synthesized according to Synthesis Scheme 5 shown below:

Scheme 5

[Chemical Formula 15]

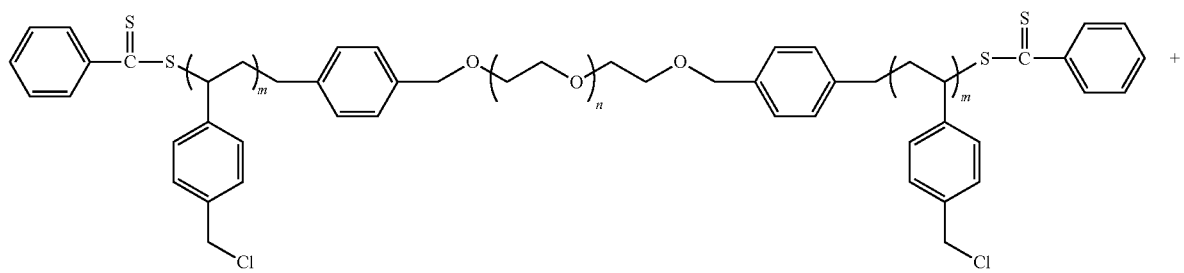

PCMS—PEG—PCMS 5 g

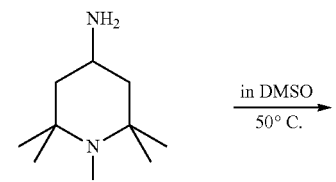

4-amino TEMPO 7.7 g in DMSO
50° C.

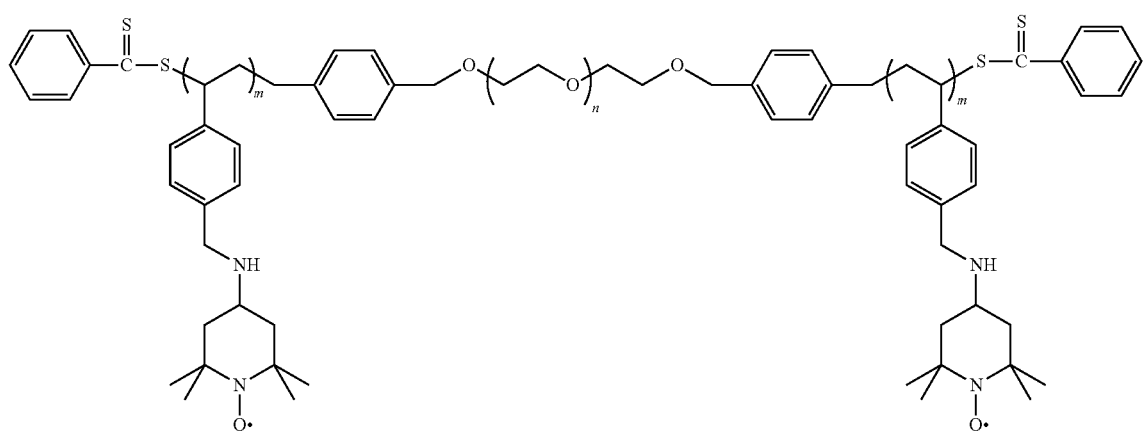

PMNT—PEG—PMNT

The target PMNT-b-PEG-PMNTb-PMNT was obtained by dissolving 5 g of the PCMS-b-PEG-b-PCMS synthesized in Production Example 2 (3) and 7.7 g of 4-amino TEMPO in DMSO and stirring at 50° C. so as to allow a reaction to progress. The obtained PMNT-b-PEG-b-PMNT was purified by being precipitated in 2-propanol and vacuum dried. The results of size exclusion chromatography (SEC) measurements and $^1$H NMR spectral measurements for the obtained polymer are shown in FIG. 7.

Working Example 1

Preparation of Polyion Complex Micelles

The powdered PMNT-b-PEG-b-PMNT triblock polymer obtained in Production Example 1 (4) was dissolved in a 0.1 M aqueous solution of HCl, the amino groups on the PMNT chains were completely protonated, and the aqueous system was freeze-dried and recovered. Next, the PMNT-b-PEG-b-PMNT triblock polymer and chondroitin sulfate (CS; Mw: 60,000) were each dissolved in a $Na_2HPO_4$ buffer solution (0.1 M) so as to prepare an aqueous cationic PMNT-b-PEG-b-PMNT solution and an aqueous anionic CS solution, each having a concentration of 5 mg/ml. Next, polyion complex micelles were prepared by adding the aqueous PMNT-b-PEG-b-PMNT solution dropwise under stirring to the aqueous CS solution while altering the pH conditions to 3.0, 4.0, 5.0 or 6.0. Here, the polyion complex micelles were prepared so that the PMNT-b-PEG-b-PMNT:CS molar ratio (r)=1:1 (molar ratio (r)=[number of moles of activated carboxyl groups in CS]/[number of moles of activated amino groups in PMNT-b-PEG-b-PMNT]). When the average particle diameter of the obtained polyion complex micelles was measured by dynamic light scattering (DLS), it was confirmed that the polyion complex micelles were unimodal particles having an average particle diameter of 45 to 60 nm. In addition, FIG. 8 shows particle size distributions.

TABLE 1

| PIC | particle diameter | PDI |
| --- | --- | --- |
| pH 3 | 57.23 | 0.127 |
| pH 4 | 59.94 | 0.108 |
| pH 5 | 53.36 | 0.111 |
| pH 6 | 47.68 | 0.131 |

Working Example 2

Preparation of Polyion Complex Micelles 100 mg of the PMNT-b-PEG-b-PMNT triblock copolymer produced in Production Example 2 (4) was dissolved in methanol, and 17.2 mg of poly(acrylic acid) (PAA; Mw: 5,000) was dissolved in water and added to the obtained methanol solution. Next, polyion complex micelles were prepared by dialyzing this solution with water. When the average particle diameter of the obtained polyion complex micelles was measured by dynamic light scattering (DLS), it was confirmed that the polyion complex micelles were unimodal particles having an average particle diameter of 31 nm (see FIG. 9).

Working Example 3

Preparation of Injectable Gel (1) 5 mg/ml of each polyion complex (PIC) micelle solution prepared in Working Example 1 was condensed by centrifugal evaporation, thereby adjusting the ionic strength to 150 mM, and gelation tests were carried out in a water bath at a temperature of 37° C. using a test tube inversion method. FIG. 10 shows photographs in place of drawings that show the results of the tests. FIG. 10 confirms that by using a PIC micelle solution having a pH of 4.0, an irreversible gel is formed at an ionic strength of 150 mM and a temperature of 37° C.

(2) In addition, the test tube inversion method disclosed in (1) was repeated, except that the polycation ($N^+$):polyanion ($COO^-$) ratio was 1:1, 2:1 or 1:2 and the pH was 5.0. FIG. 11 shows photographs in place of drawings that show these results. It was confirmed that by increasing the proportion of polycation, irreversible gelation occurred even at a pH value at which aggregation occurred (pH 5.0).

Working Example 4

Preparation of Polyion Complex Micelles 1 g of the powdered PMNT-b-PEG-b-PMNT triblock polymer obtained in Production Example 1 (2) was dissolved in a 0.1 M aqueous solution of HCl, the amino groups on the PMNT chains were completely protonated, and the aqueous system was freeze-dried and recovered. Next, the PMNT-b-PEG-b-PMNT triblock polymer and poly(acrylic acid) (PAA; Mw: 5,000) were each dissolved in a phosphoric acid buffer (0.1 M) so as to prepare an aqueous cationic PMNT-b-PEG-b-PMNT solution and an aqueous anionic PAA solution, each having a concentration of 5 mg/ml. Next, polyion complex micelles having a pH of 6.2 were prepared by adding the aqueous PMNT-b-PEG-b-PMNT triblock copolymer solution dropwise under stirring to the aqueous poly(acrylic acid) solution. Here, the polyion complex micelles were prepared so that the PMNT-b-PEG-b-PMNT:PAA molar ratio (r)=1:1 (molar ratio (r)=[number of moles of activated carboxyl groups in PAA]/[number of moles of activated amino groups in PMNT-b-PEG-b-PMNT]). When the average particle diameter of the obtained polyion complex micelles was measured by dynamic light scattering (DLS), it was confirmed that the polyion complex micelles were unimodal particles having an average particle diameter of approximately 40 to 50 nm (see FIG. 12).

Working Example 5

Preparation of Injectable Gel 5 mg/ml of each polyion complex micelle solution prepared in Working Example 4 was condensed by centrifugal evaporation, thereby adjusting the ionic strength to 150 mM, and gelation tests were carried out in a water bath at a temperature of 37° C. using a test tube inversion method. It was confirmed that by using a PIC micelle solution having a pH of 4.0 or 6.2, an irreversible gel is formed at an ionic strength of 150 mM and a temperature of 37° C. (see FIGS. 13 and 14).

<Test 1> Adhesion Prevention Performance Evaluation Test Using Redox Injectable Gel (Animal Test)

PIC micelles (pH 5, $N^+:COO^-$=2:1) prepared in the manner described in Working in Example 3 (2) were administered intraperitoneally to adhesion model mice, and the adhesion prevention effect was evaluated.

Specifically, inflammation was induced in the abdominal cavity of IGS mice (n=3, 25 to 30 g), 300 μl of talc (100 mg/ml) for causing adhesion was administered through injection into the abdominal cavity, and 1 day later, a 500 μl sample (PBS or PIC micelles (30 mg/ml)) was administered in the same way. 4 days after administration of the sample, a surgical incision was made in the abdomen of each IGS mouse, and the degree of adhesion was confirmed (FIG. 15 shows photographs in place of drawings that show the results). In cases where PBS was administered (left hand side of FIG. 15), strong adhesion was seen between organs (liver and small intestine), but it was confirmed that no adhesion was seen in mice administered with PIC micelles. From this, it can be understood that gelated PIC micelles can be used as a material that exhibits an adhesion prevention effect in a physiological environment.

<Test 2> Adhesion Prevention Performance Evaluation Test Using Redox Injectable Gel (RIG) (Animal Test)

Polyion complex micelles (pH 6.2, $N^+:COO^-=1:1$) prepared in the manner described in Working Example 4 were administered intraperitoneally to adhesion model mice, and the adhesion prevention effect and the anti-inflammatory effect of the RIG, which was determined in terms of reactive oxygen species elimination performance, were evaluated. See FIG. 16 for the experimental procedure.

Adhesion model mice were prepared by administering 300 μl of talc (100 mg/ml) as an adhesion agent to the abdominal cavity of IGS mice (n=8, 25 to 30 g) so as to induce inflammation. In order to evaluate adhesion prevention by the RIG, 300 μl of the prepared RIG (30 mg/ml) was injected into the abdominal cavity in the same way (1 day after the talc administration), and evaluations were carried out as time passed (2 days and 5 days after the talc administration). Test groups of the mice used in the present test were as follows: healthy group (non treatment), talc group (talc only administered to abdominal cavity) and talc+RIG group (RIG administered after talc administration).

Test Results 1: Adhesion Level Comparison Using Adhesion Scoring System

A surgical incision was made in the abdomen, the inside of the abdominal cavity was observed, and the degree of adhesion was classified by score in accordance with the scoring system shown in FIG. 17 (when the abdomen was lifted up using tweezers, the degree of adhesion between the abdomen and other organs was evaluated).

FIG. 18 shows the results of evaluations for each group and each score. FIG. 18 shows that significant adhesion occurred in the abdominal cavity in the talc administration group. In addition, in the results obtained after 5 days, a significant difference in adhesion score was seen between the talc administration group and the talc+RIG administration group, and it was confirmed that the RIG achieved an adhesion prevention effect.

Test Results 2: Evaluation of Reactive Oxygen Species Elimination Performance by RIG The reactive oxygen species (ROS) elimination performance of the RIG prepared in the manner described above was evaluated by means of fluorescence measurements. Specifically, abdominal wall segments were removed from the mice, the tissue was homogenized in PBS (1 ml) and then subjected to centrifugal separation (10,000 rpm, 10 min, 4° C.), 100 μl of 1 mM dihydroethidium (DHE) was added to the supernatant liquid (100 μl), and production of reactive oxygen species was quantitatively evaluated by means of fluorescence measurements (ex=530 nm, em=620 nm) (see FIG. 19).

FIG. 19 confirms that ROS were produced in the talc administration group, and production of ROS was reduced in the group to which the RIG was administered. From this, it can be understood that oxidative stress occurring at sites of inflammation can be suppressed by the RIG.

Test Results 3: Abdominal Wall Segment Thickness Measurements

It has been reported that fibers build up and abdominal wall thickness increases as neutrophils and macrophages infiltrate from sites where inflammation has occurred due to administration of talc. In this test, an abdominal wall segment is removed and immersed in 10% formalin for 1 day and a 70% ethanol for 2 days, after which 7 m of abdominal wall was cut out and stained with Masson's trichrome (MT), after which the tissue segment was subjected to observations and wall thickness measurements. The results are shown in FIGS. 20 and 21.

From these diagrams, it can be seen that significant fiber build up occurred and confirmed that inflammation occurred in the talc administration group. Meanwhile, in the talc+RIG administration group, a reduction in abdominal wall thickness was observed (a significant difference from the talc administration group was confirmed), and this suggests that the RIG exhibits an anti-inflammatory effect due to antioxidant activity.

Test Results 4: MPO Activity Evaluation

Myeloperoxidase (MPO) activity, which is known as an inflammatory biomarker, was evaluated. Abdominal wall segments were removed from mice, homogenized in 1 ml of a 50 mM phosphoric acid buffer (pH 6.0, involved 0.5% hexadecyltrimethyl ammonium bromide), and then subjected to centrifugal separation (10,000 rpm, 10 min, 4° C.). 190 μL of a 50 mM phosphoric acid buffer (pH 6), 5 μl of 0.5% o-dianisidine hydrochloride and 5 μl of 20 mM $H_2O_2$ were added to 10 μl of the supernatant liquid, after which absorption measurements (abs 460 nm) were carried out. The total protein mass in each tissue was calculated using a BCA kit (Thermo Scientific Pierce Protein Research Products), and the MPO activity per unit mass of protein was evaluated. The results are shown in FIG. 22.

From this diagram, a significant difference in terms of MPO activity can be seen between the talc administration group and the talc+RIG administration group, and it was confirmed that the RIG exhibited anti-inflammatory performance. In addition, since the diagram shows a similar tendency as compared to FIG. 19 and FIG. 21, it is thought that the antioxidant activity of the RIG contributes greatly to the anti-inflammatory activity and contributes greatly to a therapeutic effect at local sites of inflammation.

<Test 3> Adhesion Prevention Effect (Comparison with Commercially Available Separafilm*)

*Manufactured by Kaken Pharmaceutical Co., Ltd.: Film-like bioabsorbable adhesion-preventing material comprising carboxycellulose and sodium hyaluronate 300 μl of a talc dispersion (100 mg/ml) was administered into the abdominal cavity of 5 week old IGS mice (25 to 30 g). After 1 day, surgical incisions were made, the samples listed below were applied to, or placed in, the abdominal cavity, and the surgical incisions were closed. After 5 days, surgical incisions were made and organ adhesion was evaluated. See FIG. 23 for the experimental procedure.

<Samples>
Group 1: Untreated control
Group 2: Surgical incision not performed
Group 3: Surgical incision made, 300 μl of aqueous $NH_2$-TEMPO solution (6.4 mg/ml) applied to abdominal cavity, and surgical incision closed.
Group 4: Surgical incision made, nRIG (injectable gel having no antioxidant performance, 30 mg/ml aqueous solution) applied to abdominal cavity, and surgical incision closed.

Group 5: Surgical incision made, RIG (30 mg/ml aqueous solution) applied to abdominal cavity, and surgical incision closed.
Group 6: Surgical incision made, commercially available Separafilm (two sheets, 5 mm×5 mm) placed in abdominal cavity, and surgical incision closed.
Group 7: Surgical incision made, 75 μl of 6.4 mg/ml of $NH_2$-TEMPO solution applied to both surfaces of commercially available Separafilm, dried (two sheets, 5 mm×5 mm) and placed inside the abdominal cavity, and surgical incision closed.
Group 8: Surgical incision made, 75 μl of 30 mg/ml of RIG solution applied to both surfaces of commercially available Separafilm, dried (two sheets, 5 mm×5 mm) and placed inside the abdominal cavity, and surgical incision closed.

After 5 days, a surgical incision was made, adhesion to organs was scored in the manner shown in FIG. 24, and the results are shown in FIG. 25. As shown in this diagram, the RIG of the present invention and a Separafilm coated with this RIG exhibit an excellent adhesion suppression effect. The commercially available Separafilm exhibits a certain degree of adhesion suppression effect, but no significant difference was observed. Film movement was observed, and was thought to be a cause of significant variations.

Surgical incisions were then made in the treated mice, blood samples were taken, and the number of white blood cells was investigated. The results are shown in FIG. 26. The number of white blood cells in the blood was significantly lower when using the RIG and RIG-coated Separafilm, and it was understood that diffusion of inflammation throughout the body was suppressed.

5 days later, the abdominal walls were removed from the treated mice, and the quantity of reactive oxygen species, MPO activity (infiltration of neutrophils) and quantity of MDA (degree of lipid peroxidation) were quantitatively determined. The results are shown in FIGS. 27, 28 and 29. In all cases, the RIG and RIG-coated Separafilm had significantly lower measured values and exhibited excellent performance.

B. Production and Use of Ion Complex in which the Anionic Polymer in the Ion Complex of A was Replaced by One Modified so as to Bear an Indicator Production Example 3

(1) Synthesis of Poly(Acrylic Acid)-Supported Fluorescein (PAA-FL)

The PAA-FL was synthesized according to Synthesis Scheme 5 shown below.

[Chemical Formula 16]

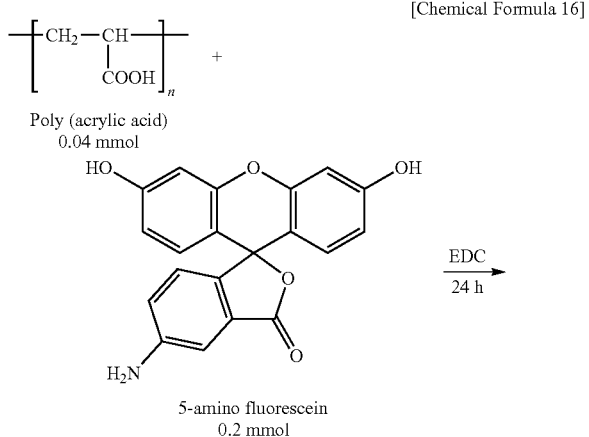

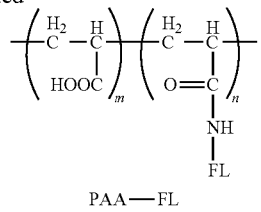

0.04 mmol of a poly(acrylic acid) (molecular weight 5,000 g/mol) was dissolved in 5 ml of $H_2O$, and 0.2 mmol of 5-aminofluorescein was dissolved in 5 ml of DMSO. These 2 solutions were mixed, and 0.4 mmol of 1-ethyl-3-(3-dimethylaminopropyl)carbodiimide hydrochloride (EDC) was added and stirred for 24 hours. Next, a 0.1 M HCl solution was added so as to adjust the pH to 7.0, the solution was placed in a dialysis membrane (MWCO=3,500) and dialyzed with 2 L of water, and unreacted aminofluorescein was removed. The water was replaced 8 times at intervals of 2 hours, the solution was freeze dried by freeze drying the aqueous system, and PAA-FL was recovered. The synthesized PAA-FL was dissolved in a phosphoric acid buffer, purification of the dissolved PAA-FL was confirmed by passing through a PD10 column, and it was confirmed that unreacted aminofluorescein was removed.

(2) Preparation of Redox Injectable Gel-Supported Fluorescein (FL-RIG)

A PMNT-b-PEG-b-PMNT triblock copolymer (in formula I above, $L_1$ is —S—$CH_2$—, $L_2$ is —$CH_2$—NH—, R is a group derived from 4-amino-TEMPO, Y is hydrogen, m is approximately 22, and n is approximately 454), which was synthesized according to the method disclosed in WO 2013/111801, and PAA-FL were each dissolved in a phosphoric acid buffer (0.1 M), thereby preparing an aqueous cationic PMNT-b-PEG-b-PMNT solution adjusted to a concentration of 5 mg/ml and an aqueous anionic PAA-FL solution adjusted to a concentration of 5 mg/ml. Next, polyion complex micelles having a pH of 6.2 were prepared by adding the prepared aqueous PMNT-b-PEG-b-PMNT triblock copolymer solution dropwise under stirring to the aqueous poly(acrylic acid) solution. Here, the polyion complex micelles were prepared so that the PMNT-b-PEG-b-PMNT:PAA molar ratio (r)=1:1 (molar ratio (r)=[number of moles of activated carboxyl groups in PAA]/[number of moles of activated amino groups in PMNT-b-PEG-b-PMNT]).

<Gelation>

The polyion complex micelle solution (5 mg/ml) prepared in the manner described above was concentrated (to 30 mg/ml) by centrifugal evaporation, the ionic strength was adjusted to 150 mM, and a gelation test was carried out in a water bath at a temperature of 37° C. using a test tube inversion method.

Moreover, FIG. 30 is a conceptual diagram relating to Production Example 3 (2) and gelation.

The results of this test confirmed that irreversible gelation occurred at 37° C. (see FIG. 31). For purposes of comparison, a redox nanoparticle solution (30 mg/ml) was prepared using a similar procedure from a PEG-b-PMNT polymer (a polymer disclosed in WO 2009/133647 or produced using a method disclosed in WO 2009/133647) and PAA-FL. The aqueous solution in this comparative example did not exhibit gelation behavior under physiological conditions in the gelation test described above.

<Test 4> Evaluation of Retention in Abdominal Cavity of Redox Injectable Gel (RIG-FL) Obtained in Production Example 3 (2) (Evaluation of Retention in Abdominal Cavity of RIG Using IVIS Imaging)

Using a solution of redox nanoparticles on which a low molecular weight fluorescent substance (aminofluorescein: AFL) and FL were supported (FL-RNP) and a redox injectable gel on which FL was supported (FL-RIG), retention in abdominal cavity was evaluated according to the following scheme.

Using nude mice (n=4, 25 to 30 g), a test was carried out by administering IVID#2, which was purchased from Oriental Yeast Co., ltd., 1 week before the start of the test in order to prevent deflection of fluorescence from the feed. Under anesthesia induced by inhalation of isoflurane, a surgical incision was made in the abdomen of each mouse, 300 μl of a sample (AFL, FL-RNP (micelle concentration 30 mg/ml) or FL-RIG (micelle concentration 30 mg/ml)) was administered, and the abdomen was sutured. The method for evaluating retention in the abdominal cavity involved imaging fluorescence from the fluorescein (excitation wavelength: 500 nm, fluorescence wavelength: 540 nm) supported by the sample at timing points immediately after administration, and evaluating the quantity of sample remaining in the abdomen by quantitatively determining the reduction in fluorescence from the fluorescence intensity measured immediately after administration. The imaging was carried out with the mice under anesthesia by isoflurane. FIG. 32 shows images for the samples, and FIG. 33 shows quantitative determination data that shows the sample quantities remaining. In the RIG administration group, retention in the abdominal cavity was improved by gelation, and a significant difference from the control groups (AFL, FL-RNP) was observed. These results suggest that the prepared RIG suppresses contact between tissues in the abdominal cavity and exhibits good functionality as an adhesion prevention agent.

INDUSTRIAL APPLICABILITY

Because it can be understood that polyion complex micelles of the present invention have been confirmed as exhibiting an adhesion prevention effect, as disclosed in the description of the present application, the present invention can be used to produce and market an adhesion-preventing preparation able to be used in medical care.

The invention claimed is:

1. A method for preventing adhesion of tissues or organs in a living body, comprising administering a composition comprising a triblock copolymer and a polyanionic polymer to a site in a living body that requires administration, at a quantity that is effective to prevent adhesion of tissues or organs of a patient, wherein the triblock copolymer is represented by formula (II), (II)

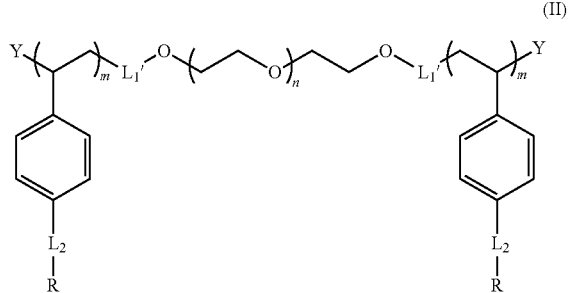

wherein:

$L_1'$ is each independently selected from the group consisting of

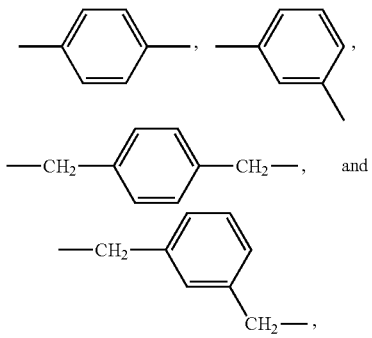

$L_2$ is each independently a $-C_{1-6}$ alkylene-NH—$(C_{1-6}$ alkylene$)_q$- group, wherein q is an integer of 0 or 1, R is each independently a group such that at least 20% of the total number (n) of R groups are residues of cyclic nitroxide radical compounds selected from the group consisting of 2,2,6,6-tetramethylpiperidin-1-oxyl-4-yl groups, 2,2,5,5-tetramethylpyrrolidin-1-oxyl-3-yl groups, 2,2,5,5-tetramethylpyrrolin-1-oxyl-3-yl groups, 2,4,4-trimethyl-1,3-oxazolidin-3-oxyl-2-yl groups, 2,4,4-trimethyl-1,3-thiazolidin-3-oxyl-2-yl groups and 2,4,4-trimethyl-imidazolidin-3-oxyl-2-yl groups, wherein the remaining R groups, when present, are hydrogen atoms, halogen atoms or hydroxyl groups, Y is each independently selected from the group consisting of hydrogen, a phenylthiocarbonylthio group optionally substituted by a $C_{1-6}$ alkyl group, a $C_{1-6}$ alkylthiocarbonylthio group and a $C_{1-6}$ alkyloxythiocarbonylthio group, each m is independently an integer between 3 and 1000, and n is an integer between 20 and 5000, and the anionic polymer is one or more types selected from the group consisting of a poly(acrylic acid), a poly(methacrylic acid), a poly(sulfonic acid), a polyanionic polysaccharide and an anionic protein.

* * * * *